United States Patent
Weir

(10) Patent No.: US 9,788,989 B2
(45) Date of Patent: Oct. 17, 2017

(54) NASAL DILATOR

(71) Applicant: Kenneth Ray Weir, Corpus Christi, TX (US)

(72) Inventor: Kenneth Ray Weir, Corpus Christi, TX (US)

(*) Notice: Subject to any disclaimer, the term of this patent is extended or adjusted under 35 U.S.C. 154(b) by 0 days.

(21) Appl. No.: 14/432,934

(22) PCT Filed: Oct. 4, 2013

(86) PCT No.: PCT/US2013/063499
§ 371 (c)(1),
(2) Date: Apr. 1, 2015

(87) PCT Pub. No.: WO2014/058740
PCT Pub. Date: Apr. 17, 2014

(65) Prior Publication Data
US 2015/0230965 A1 Aug. 20, 2015

Related U.S. Application Data

(60) Provisional application No. 61/711,445, filed on Oct. 9, 2012.

(51) Int. Cl.
A61F 5/08 (2006.01)
A61F 5/56 (2006.01)

(52) U.S. Cl.
CPC . *A61F 5/08* (2013.01); *A61F 5/56* (2013.01)

(58) Field of Classification Search
CPC ...... A61F 5/08; A61F 5/56; A61F 5/30; A61F 5/32; A61F 5/34; A61F 5/37; A63B 33/002; A63B 2033/004; A63B 2033/006; A63B 2033/008
See application file for complete search history.

(56) References Cited

U.S. PATENT DOCUMENTS

| | | | |
|---|---|---|---|
| 4,774,935 A | 10/1988 | Aronsohn | |
| 6,860,263 B1* | 3/2005 | Scoggins | A61F 5/08 128/200.24 |
| 7,055,523 B1* | 6/2006 | Brown | A61F 5/08 128/206.11 |
| 2004/0111109 A1* | 6/2004 | Ruiz | A61F 5/08 606/199 |
| 2008/0119885 A1 | 5/2008 | Yazdi | |
| 2009/0025715 A1 | 1/2009 | Sugden | |
| 2009/0183734 A1 | 7/2009 | Kwok | |
| 2010/0307502 A1* | 12/2010 | Rummery | A61M 16/06 128/205.25 |
| 2012/0160240 A1 | 6/2012 | Spano | |

\* cited by examiner

*Primary Examiner* — Jocelin Tanner
(74) *Attorney, Agent, or Firm* — M. Susan Spiering; Ferrells, PLLC

(57) ABSTRACT

A simple, reusable, adjustable nasal dilator is disclosed for improved breathing by the user. The dilator includes first and second elastic bands to which nose clips are attached. The nose clips are used for engaging with the side walls of the user's nostrils, and optionally have nose pads for increased comfort level during use. The two bands of the dilator work together to pull the user's nostrils open, thereby providing force and tension to dilate the nasal passages of the user. The nasal dilator can be worn during sleep periods to improve breathing and sleeping, as well as other times the user wishes to improve air flow through the nasal passages.

13 Claims, 3 Drawing Sheets

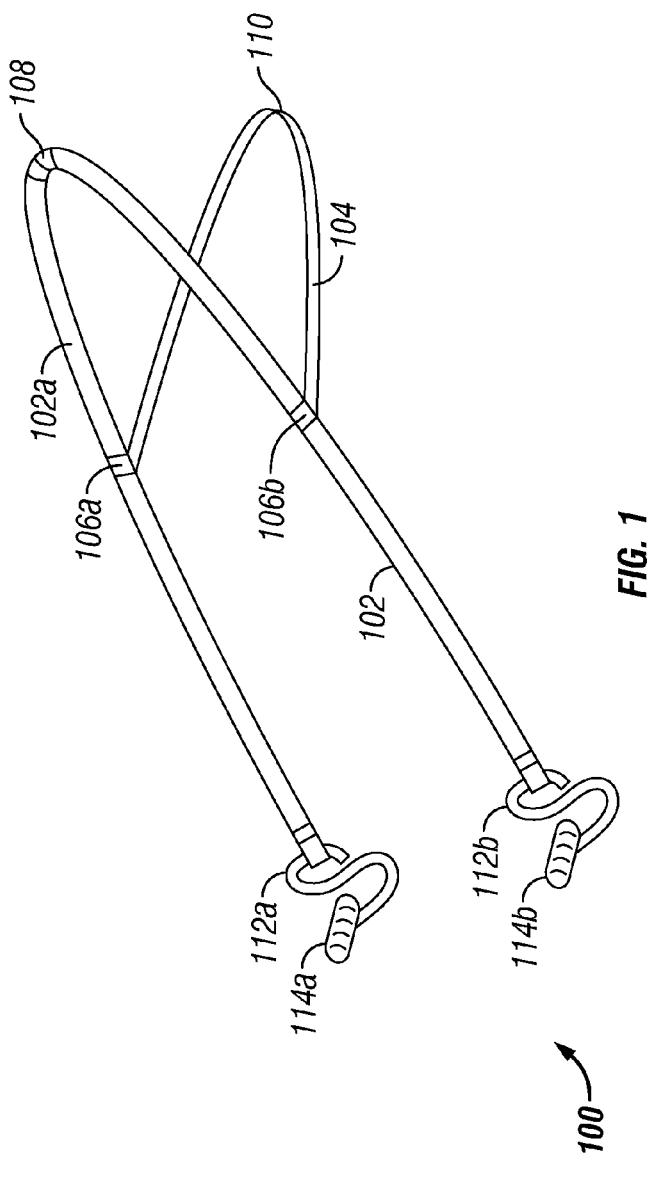
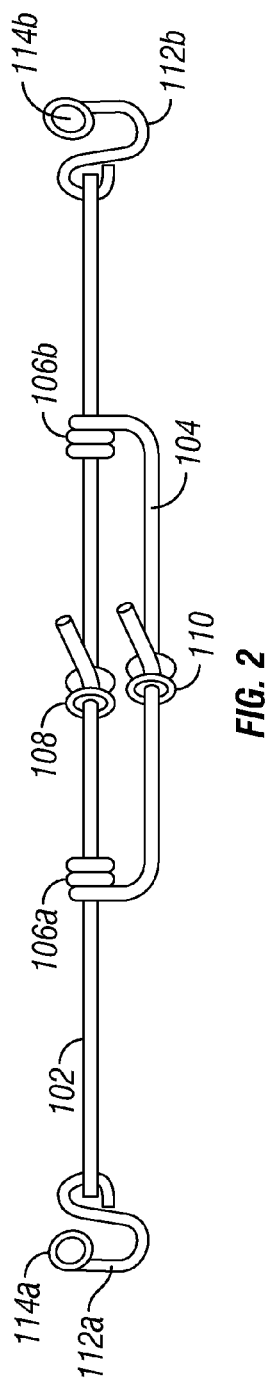
FIG. 1
FIG. 2

NASAL DILATOR

CROSS REFERENCE TO RELATED APPLICATIONS

This international patent application is based on U.S. Provisional Patent Application Ser. No. 61/711,445, entitled, "Nasal Dilator", filed Oct. 9, 2012, the priority of which is hereby claimed and the disclosure of which is incorporated herein by reference in its entirety.

BACKGROUND

Field of the Invention

The present invention relates generally to medical instruments. More particularly, the present invention relates to a nasal dilator to be used as a breathing aid.

Description of the Related Art

Due to health problems, such as deviated septa, obesity, allergies, cold, congestion, and medications used for said health problems and others, many people suffer from breathing problems. They are not able to breathe efficiently through their nose due to the restricted nasal passages, and are prone to breathe through their mouth.

Hospital studies have established that nocturnal mouth breathing is a primary cause of loud snoring. Snoring is a precursor to sleep apnea and apnea a precursor to heart attacks which, can result in dying in one's sleep. Published western clinical evidence clearly proved that mouth breathing, is one of two immediate leading causes of mortality in the severely sick due to chronic diseases. Due to the lack of proper oxygenation, the ability to deliver fully oxygenated blood to the cells is also much reduced. Thus mouth breathing has a negative effect on every cell in the body as it deprives them of oxygen. Overall wellness and health requires proper oxygen as every particle of our being requires oxygen. Cancer cells, by the way, are anaerobic (living in the absence of oxygen) by design. In contrast, proper nose breathing delivers fully oxygenated blood to the body, reduces hypertension and stress, and promotes cardiovascular heath. The nostrils and sinuses filter and warm the air that enters the lungs. Thus, proper nose breathing is essential for wellbeing of humans.

Conventional nose breathing aids provide temporary relief from restricted breathing. Traditional aids include nasal sprays, and various types of nasal dilators, sinus cones, nasal strips, and springs to hold nasal passages open. For example, U.S. Pat. No. 6,860,263 by Al Scoggins discloses a cheek tape having adhesive for pulling the nasal cavity open during use. These items have various names on the market. In addition, there exists nose mounted dilators wherein adhesive is used to adhere the dilator to the user's face or nose. The nose mounted dilator includes a resilient bar having an adhesive portion on either end. When the adhesive portions are attached to the side walls of the nose, the bar is bent and attempts to spring back into a straightened state, which in turn pulls the nostrils apart, thereby diluting the nasal passages and providing breathing relief to the user.

However, the adhesive portions on the nose mounted dilator tend to lose sticking power due to secretion of oils from the nose. Further, the nose mounted dilator is not suitable for wearing during long periods of exercise, as the adhesive portions lose sticking power due to excessive sweating. The quality of adhesive portions of the dilator generally restricts it to being a onetime use, disposable type product.

U.S. patent application 2012/0160240 by Michael J. Spano discloses a sleep mask that integrates a nasal dilator. The nasal dilation element includes a channel through which a band can move substantially orthogonal to the wearer's nose. Sidewalls center the band and inward folded cuffs retain the band. Such bands are complex in construction, expensive, and fell to provide the force required for adequately palling the wearer's nostrils and retaining the dilator in place.

There exists nasal dilators that also clip to the nasal septum (the divider between the nostrils), or slid into the nasal passage, and are sold under the trade names: Clip Air®, Breathe EZ™, Breathe Quiet, Max-Air, Nasilator, Brez, Nosovent, Respirn, Sinus Cones, Sleep Right, Breathe-ezy Nasal Filters, and Nasaline®, among others.

The disadvantage of most nose mounted dilators mounted inside the nasal cavity, is that while most of them do actually dilate the nasal passages, the product itself becomes a new obstruction, and is most noticeable during exhalation. Upon exhalation, the user will experience the deflection of hoi breath against the apparatus. Consequently, this apparatus can become bothersome, and will generally not be worn for extended periods of time, thereby forfeiting the benefits of enhanced nose breathing.

In light of the foregoing, there exists a continued need for a simple, economical, non-medicated forms of nasal breathing relief, to provide a solution that overcomes the above mentioned problems associated with the prior art alternatives.

SUMMARY

An object of the present invention is to provide a breathing aid to open the nasal passages and enhance breathing both during inhalation and exhalation.

Another object of the present invention is to provide a breathing aid that is durable and can be easily worn during physical activities.

Embodiments of the present invention provide a nasal dilator, which includes a first elastic band having two ends, a pair of nose clips, a pair of optional nose pads, and a second elastic band attached to the first elastic band. Each nose clip is attached to an end of the elastic band and configured to engage with an inside wall of a nostril of a user of the nasal dilator. Each nose pad is attached to an end of a nose clip for pressing against an inside wall of a nostril of the user. The second elastic band has two ends attached to two attachment points of the first elastic band. The first elastic band between the two attachment points is configured to be wrapped around an upper back portion of a user's head. The second elastic band is configured to be wrapped around a lower back portion of a user's head. The first elastic band is configured to apply a pulling force on the nose clips for pulling the user's nostrils apart, thereby allowing the nasal passages to dilate. The second elastic band serves as an additional tensioning point, and also secures the first band in place during an entire night's sleep, or during extended use during the day.

Further aspects and advantages of the invention will become apparent from the discussion which follows.

BRIEF DESCRIPTION OF THE DRAWINGS

The present invention is described in connection with the attached Figures, wherein:

FIGS. 1-4 illustrate schematic diagrams of different views of the nasal dilator;

DETAILED DESCRIPTION OF THE EMBODIMENTS

Figure 3:
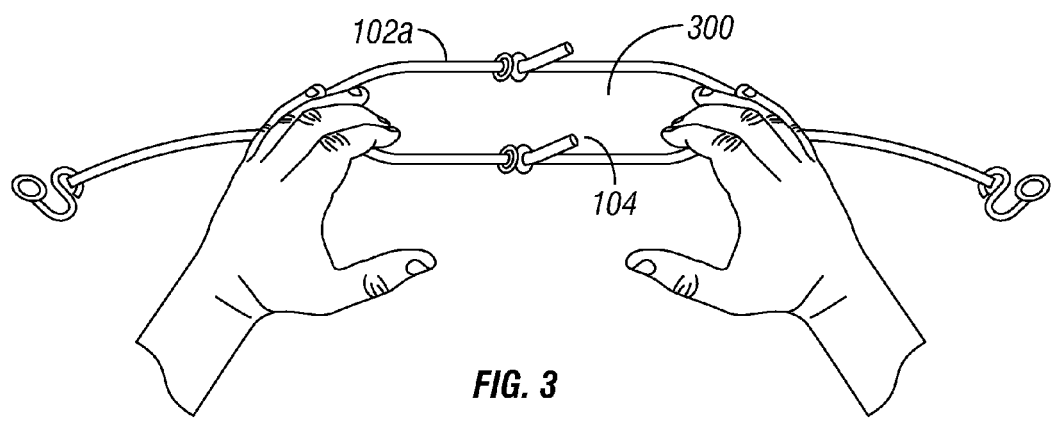

The invention is described in detail below with reference to several embodiments and numerous examples. Such discussion is for purposes of illustration only. Modifications to examples within the spirit and scope of the present invention, set forth in the appended claims, will be readily apparent to one of skill in the art. Terminology used throughout the specification and claims herein is given its ordinary meaning as supplemented by the discussion immediately below. As used in the specification and claims, the singular forms "a", "an" and "the" include plural references unless the context clearly dictates otherwise.

Those with ordinary skill in the art will appreciate that the elements in the Figures are illustrated for simplicity and clarity and are not necessarily drawn to scale.

There may be additional components described in the foregoing application that are not depicted on one of the described drawings. In the event such a component is described, but not depicted in a drawing, the absence of such a drawing should not be considered as an omission of such design from the specification.

Before describing the present invention in detail, it should be observed that the present invention provides a nasal dilator. Accordingly, components of the nasal dilator have been represented where appropriate by conventional symbols in the drawings, showing only specific details that are pertinent for an understanding of the invention so as not to obscure the disclosure with details that will be readily apparent to those with ordinary skill in the art having the benefit of the description herein.

As required, detailed embodiments of the present invention are disclosed herein; however, it is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. Further, the terms and phrases used herein are not intended to be limiting but rather to provide an understandable description of the invention.

Referring now to FIG. 1, a nasal dilator 100 for use as a breathing aid, in accordance with an embodiment of the present invention, is shown. The nasal dilator 190 includes a first elastic band 102, a second elastic band 104 attached to the first elastic band 102, and a pair of nose clips 112a and 112b, each attached to an end of the first elastic band 102. For example, the nose clip 112a is attached to one end and the nose clip 112b is attached to another end of the first elastic band 102. Each of the nose clips 112a and 112b is configured to engage with a side wall of a nostril of a user of the nasal dilator 100.

The nasal dilator 100 further includes coiled metal, or optional silicone nose pads 114a and 114b attached to ends of the nose clips 112a and 112b respectively. Each coiled metal, or optional silicone nose pad 114a and 114b is configured to press against a side wall of a nostril of the user, when the nose clips 112a and 112b are engaged to the side walls of user nostrils.

The second elastic band 104 includes two ends attached to two attachment points 106a and 106b of the first elastic band 102. For example, one end of the second elastic band 104 is attached to the attachment point 106a and another end is attached to the attachment point 106b.

In one embodiment of the present invention, the attachment points 106a and 106b are tension and positioning adjustment points, which enable a tension adjustment in the first and second elastic bands 102 and 104.

The first elastic band 102 comprises a strap adjuster 108 and the second elastic band 104 comprises a strap adjuster 110. The strap adjusters 108 and 110 are configured to adjust lengths of the first and second elastic bands 102 and 104 respectively. Such strap adjusters are well known in the art and their description has been omitted from the present specification.

In use, the first elastic band 102a, located between the two attachment points, 106a and 106b, is wrapped around the upper back portion of a user's head. The second elastic band 104 is wrapped around the lower back portion of the user's head. When the first and second elastic bands, 102 and 104, are wrapped around the user's head, band 102 applies a pulling force on the nose clips 112a and 112b, pulling the user's nostrils apart, thereby allowing the nasal passages to dilate.

Materials for the elastic bands can be varied provided they have elasticity and provide some comfort in wear to the user. The bands 102 and 104 can be made from elastic banding as found in traditional sewing stores, or from stretch fabrics or materials such as neoprene, or other vinyl based, rubber material. The nose clips 112a and 112b may be made from metal, stainless steel or resilient plastic. The nose pads 114a and 114b may be coiled metal or made from optional silicone, plastic, or a metal with rubberized coating. The strap/band adjusters 108 and 110 may be made from plastic or metal.

The first and second elastic bands 102 and 104 are shown herein formed separately and then joined at the attachment points 106a and 106b. However, they can be integrally formed together and function as well.

In one embodiment, the nose clips (112a, 112b) and the corresponding nose pads (114a, 114b) are manufactured separately using different materials, and joined thereafter employing a suitable process. In another embodiment, the nose clips (112a, 112b) and the corresponding nose pads (114a, 114b) are integrally formed using a single material such as coiled metal, or resilient plastic.

As described and shown herein, the nose clips 112a and 112b have an elongated "S" shape. However, other possible shapes of the nose clips are possible, and are within the scope of the present invention. For example, the nose clips can be an elongated "C" shape with an attachment point for the elastic strap, and coiled metal for comfortable contact point with the nostril.

Referring to FIG. 2, the nasal dilator 100 illustrates the attachment points 106a and 106b, between the first elastic band 102, and the second elastic band 104. This view also illustrates the strap adjusters, 108 and 110, for increasing/decreasing the length of the bands (102 and 104 respectively).

Referring to FIG. 3, a third view of the nasal dilator 100 is shown. Here, the user pulls apart the first elastic band, 102a, between the two attachment points, 106a and 106b, and the second elastic band, 104, for preparing a loop 300. The loop 300 is configured to be wrapped around the head of the user.

Figure 4:
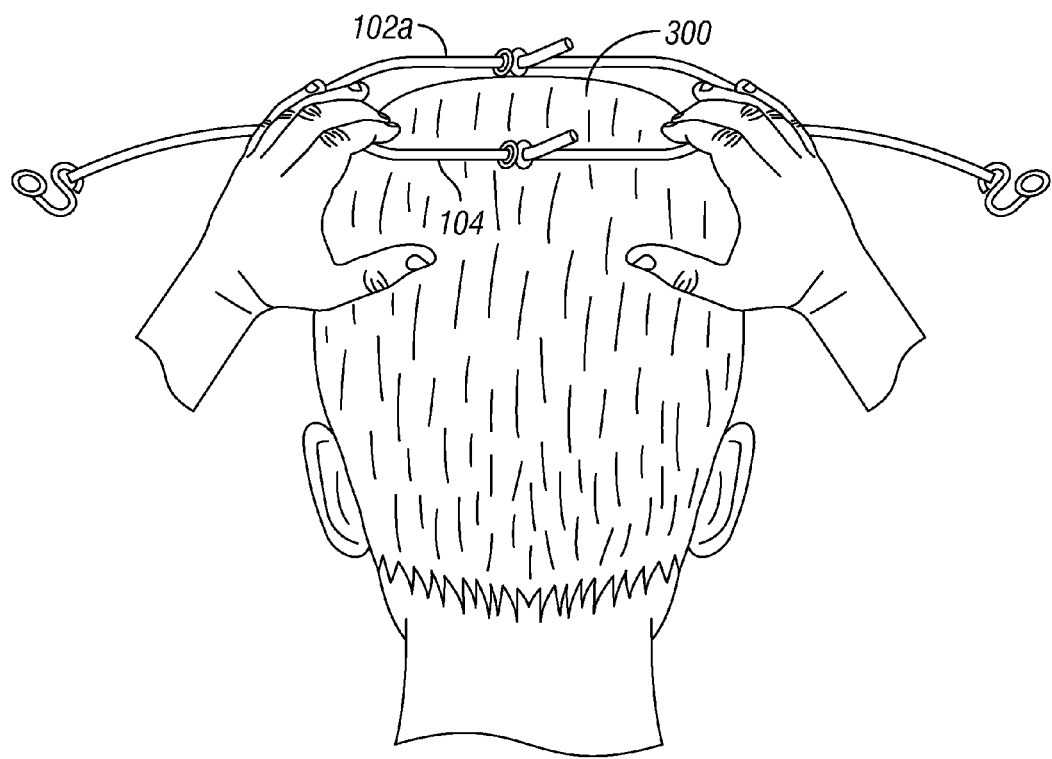

Referring to FIG. 4, a fourth view of the nasal dilator 100, is shown. The loop 300 is configured to be fitted around the user's head for wrapping the first elastic band 102a around the top back portion, and the second elastic band, 104, around the lower back portion, of the user's head.

Figure 5:
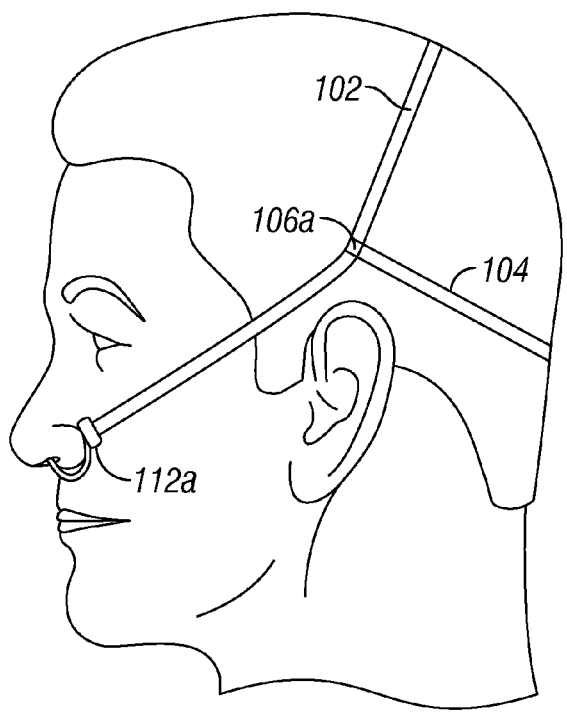
FIG. 5 is a schematic diagram which illustrates a side view of a user's head wearing the nasal dilator.

Referring to FIG. 5, a side view of the user's head wearing the nasal dilator is shown. The first elastic band 102 is shown to be wrapped around the top back portion of the user's head, and the second elastic band, 104, is shown to be wrapped around the lower back portion of the user's head. The nose clips 112a is illustrated, engaged to the inside walls of the user's nostril.

As shown in FIG. 5, the first elastic band, 102, rests on the upper cheek bone, crosses a temporal region, and then wraps around a perientel bone of the user. The second elastic band 104 attaches in the temporal region, and then wraps around an occipital bone of the user.

The first elastic band, 102, is shown to be supported by the second elastic band, 104. The second elastic band 104 keeps the first elastic band 102 securely positioned at its place, especially during night time movements of the user while sleeping, or during physical activity.

The attachment points 106a and 106b, (only one attachment point 106a shown in the figure), can be slid forward or backward to apply gentle tension force on the side of each nostril to dilate the nasal passages. The resulting tension of the bands 102 and 104 causes the nostrils to gently move outward, thereby creating dilation in both nostrils and thus in the nasal passages. The attachment points 106a and 106b provide the final tensioning and positioning adjustment for suitably dilating the nasal passages.

Figure 6:
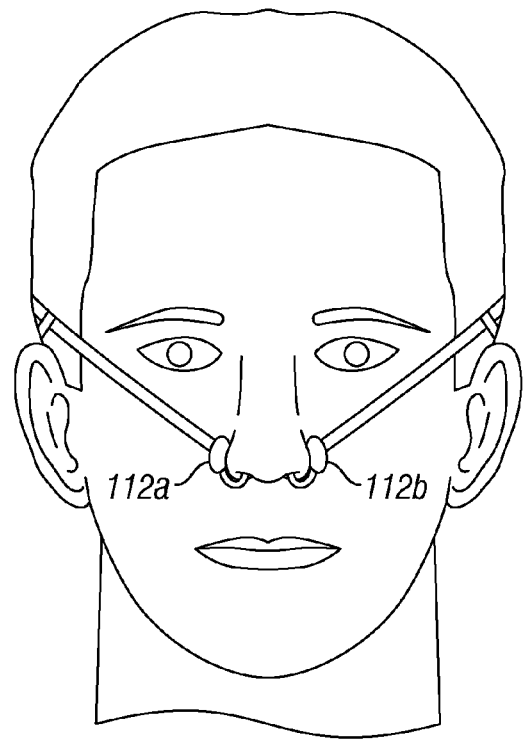
FIG. 6 is a schematic diagram which illustrates a front view of the user's head wearing the nasal dilator.

FIG. 6 illustrates a front view of the user's head wearing the nasal dilator wherein, the first and second elastic bands 102 and 104 apply a pulling force on the nose clips 112a and 112b for pulling the user's nostrils apart, thereby allowing the nasal passages to dilate.

To obtain the force measurements, several methods were used:

A metal clip was fitted with the band used for the Nasal dilator. A ¼" wide and 5" long braided polyester band was attached to the clip. Then a strip of masking tape was measured with markings from 0" to 1" and adhered to the cheek bone from the nostril to the hairline beneath the normal travel of the Nasal dilator head band. 0" to 1" was also measured and marked on the elastic band. The clip was then placed in the nostril. The markings on the elastic band and masking tape were aligned so that the zero and one inch markings lined up with each other. Then tension was applied to the elastic band to dilate the nasal passage. Once proper dilation was obtained, the 1" marked on masking tape was marked on the elastic band.

A second stretch/tension test was conducted as described above, using a household rubber band, and the same 0" to 1" markings were placed on the rubber band. Then when tension was applied to the rubber band to achieve dilation, the amount of stretch required was measured with the markings on the masking tape vs the markings on the rubber band. The new 1" mark was transferred to the rubber band. Then small weights were added to the clip while holding the clip away from the face and up against another 0" to 1" scale. When the markings lined up with the markings of the stretched rubber band, the weights were removed and placed on a postal scale. The test measured 2.8 oz weight/pressure.

A third test was performed using a digital dynomometer that would measure 1 oz to 50 lbs. A metal clip was placed to the nostril and attached to the dynomometer. Using the handheld dynomometer, tension was applied to the metal clip dilating the nostril This test measured 2.75 oz. Then clips were placed in each nostril with a non-elastic band wrapped around the head. The handheld dynomometer was hooked to the band in the back of the head, and then pulled outward to pull the nostrils outward and dilate the nasal passages. When proper dilation was acquired, the measurement on the dynomometer was noted. This test measured 5.5 oz.

The dynomometer measured both kg and lbs, and the above tests were performed measuring both kg and then lbs.

In an exemplary embodiment of the present invention, the first and second elastic bands 102 and 104, hereinafter collectively referred to as the head band, are made of about ¼" wide braided polyester. The width and elasticity of the head band can vary as long as it can provide a tension of about 5 to 7 oz. The ¼" wide band provides optimum elasticity and adjustability; however a ⅜" or wider band is less prone to twisting or tangling when not in use. The head band can be made of various widths and elasticity.

The total force required tor proper nasal dilation of both nostrils was found to be about 0.1559 kg., 0.34375 lbs., or 5.5 oz. The force required to dilate just one nostril is about half the total, i.e. 0.0780 kg., 0.1718 lbs., or 2.75 oz. Proper dilation requires at least the side nostril wall to be stretched outward approximately ¼". The head band, when wrapped around the head and properly adjusted, only has approximately a 0.50 in. (about ½") stretch to clip into each nostril. This selling has a minimal tension, i.e., 5.5 oz., was found to be comfortable, and can be worn throughout the entire night, or as long as desired for daytime activities including spotting and/or physical activities. Generally, it has been found that a starting range of pulling force tor adequate dilation of at least one of the nasal passages is in the range of about 0.065 kg to about 0.160 kg, preferably about 0.078 kg to about 0.1559 kg. It is anticipated that the wearer will find the optimum pulling force range with minimal trial and error.

The force found to fully extend the nostrils open was about 0.46 kg., 1.014 lbs, or 16.23 oz. It has been found that extending the nostrils beyond about a ¼ inch provides minimal to no improvement of the dilation of nasal passages, and provides some user discomfort. The proper adjustment of tension for the majority of users is approximately 5.5 oz., which will extend each nostril approximately ¼ inches. However it will be recognized that people vary in head size and size of nasal passages, thus the force required for dilation can vary. Factors varying the amount of force required for dilation also can include, but not be limited to, the user's health, weight, severity of deviated septum, if applicable, and thickness of nostril walls.

Various embodiments of the present invention offer one or more of the following advantages:

Nasal passages remain dilated even during facial contortions such as talking, eating, coughing, sneezing, yawning, and most bed/pillow to head/face contact points. The nasal dilator creates a substantially increased volume of airflow in people with restricted nasal passages and can be easily adjusted and re-used. In addition, the nasal dilator remains in place during night time movement, such as turning and rotating head during sleep, or even more intense exercise routines. Moreover, the tension on the bands 102 and 104 can be easily adjusted for maximum or minimum nasal dilation.

While the invention, has been described in detail, modifications within the spirit and scope of the invention will be readily apparent to those of skill in the art. Such modifications are also to be considered as part of the present invention. In view of the foregoing discussion, relevant knowledge in the art and references or information discussed above in connection with the Background of the Invention, the disclosures of which are all incorporated herein by reference, further description is deemed unnecessary, in addition, it should be understood that aspects of the invention and portions of various embodiments may be combined or interchanged either in whole or in part. Furthermore, those of ordinary skill in the art will appreciate that the foregoing description is by way of example only, and is not intended to limit the invention.

Thus, the present invention has been described herein with reference to a particular embodiment for a particular application. Although, selected embodiments have been illustrated and described in detail it may be understood that various substitutions and alterations are possible. Those having ordinary skill in the art and access to the present teachings may recognize additional various substitutions and alterations are also possible without departing from the spirit and scope of the present invention, and as defined by the following claims.

What is claimed is:

1. A nasal dilator, comprising:
a first elastic band having two ends;
a pair of S-shaped nose clips, wherein each S-shaped nose clip has a first and second end and one end is attached to an end of the elastic band and configured to engage with a respective inside wall of a nostril of a user;
a pair of nose pads, wherein each nose pad is attached to an opposite end of the respective S-shaped nose clip for pressing against the respective side wall of the nostril of the user, said nostril attached to nasal passages; and
a second elastic band attached to the first elastic band, wherein the second elastic band has two ends attached to two attachment points of the first elastic band, wherein the first elastic band between the two attachment points is configured to be wrapped around an upper back portion of a user's head and the second elastic band is configured to be wrapped around a lower back portion of the user's head, and wherein the first elastic band is configured to apply a pulling force in the range of 0.065 kg to 0.160 kg on the S-shaped nose clips for outwardly stretching the user's nostrils apart, thereby allowing the nasal passages to dilate;
wherein further the first elastic band is configured to be wrapped around a parietal bone of the user and the second elastic band is configured to be wrapped around an occipital bone of the user, serving as an adjustable tension point and to secure the first band in place during a user's sleep period.

2. The nasal dilator of claim 1, wherein each of the first and second elastic bands comprises a strap adjuster for adjusting a length thereof.

3. The nasal dilator of claim 1, wherein the attachment points are tension and positioning adjustment points, enabling a tension adjustment in the first and second elastic bands for dilating the nasal passages.

4. The nasal dilator of claim 1, wherein the first and second elastic bands are made from a material selected from a group consisting of elastic, neoprene, and rubber.

5. The nasal dilator of claim 1, wherein the S-shaped nose clips are made from a material selected from a group consisting of metal, stainless steel, and resilient plastic.

6. The nasal dilator of claim 1, wherein the nose pads are made from a material selected from a group consisting of silicone, plastic, and metal with rubberized coating.

7. The nasal dilator of claim 6, wherein the nose pads are made from a material selected from a group consisting of silicone, plastic, and metal with coiled metal.

8. The nasal dilator of claim 1, wherein the nasal dilator is used for dilating restricted nasal passages of the user during talking, eating, coughing, sneezing, yawning, exercising, and sleeping.

9. The nasal dilator of claim 1, wherein the pulling force for dilating the nasal passages is calculated based on the size of the user's head, a size of nasal passages, and type of nasal cavities.

10. The nasal dilator of claim 9, wherein the pulling force for dilating both nasal passages is equal to about 0.1559 kg.

11. The nasal dilator of claim 10, wherein the pulling force for dilating a single nasal passage is equal to about 0.078 kg.

12. The nasal dilator of claim 1 wherein the pulling force for dilating at least one nasal passage is in the range of about 0.065 kg to about 0.160 kg.

13. The nasal dilator of claim 12 wherein the pulling force for dilating at least one nasal passage is in the range of about 0.078 kg to about 0.1559 kg.

* * * * *